US00PP30530P2

(12) United States Plant Patent
Egger

(10) Patent No.: US PP30,530 P2
(45) Date of Patent: May 21, 2019

(54) ***AGASTACHE* PLANT NAMED 'TNAGAPL'**

(50) Latin Name: ***Agastache* hybrid**
Varietal Denomination: TNAGAPL

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/932,028

(22) Filed: Jan. 25, 2018

(51) Int. Cl.
*A01H 5/02* (2018.01)

(52) U.S. Cl.
USPC ..... Plt./399
CPC ..... *A01H 5/02* (2013.01)

(58) Field of Classification Search
USPC ..... Plt./399
See application file for complete search history.

*Primary Examiner* — Anne Marie Grunberg
(74) *Attorney, Agent, or Firm* — Klarquist Sparkman, LLP

(57) ABSTRACT

A new and distinct form of *Agastache* plant is disclosed, characterized by lavender pink flowers in large inflorescences, a long bloom time, a short, compact habit, good cold tolerance, and excellent vigor.

1 Drawing Sheet

Botanical denomination: *Agastache* hybrid.
Variety designation: 'TNAGAPL'.
Trademark designation: Poquito™ Lavender.
Comparison to sibling *Agastache* 'TNAGAPDB'.

BACKGROUND OF THE INVENTION

The present invention relates to a new and distinct cultivar of *Agastache*, given the name, 'TNAGAPL'. *Agastache* is in the family Lamiaceae. This new cultivar is one of several selections of new *Agastache* using hardy and dwarf *Agastache* species in the breeding lines to provide hardiness and compactness. The new cultivar is a selection from the open pollinated seedlings of *Agastache* '66-04', a proprietary, unpatented seedling. The new cultivar was selected for its compact habit, hardiness, and lavender pink flowers.

Compared to the seed parent, *Agastache* '66-4' the new cultivar is shorter with better branching and lavender pink rather than purple blue flowers.

Compared to its sibling, *Agastache* 'TNAGAPDB', U.S. Plant Pat. No. 28,950, the new cultivar has a lower, broader habit and lavender pink flowers rather than purple blue.

Compared *Agastache* 'Kudos Ambrosia' (U.S. Plant Pat. No. 25,614), the new cultivar is shorter with rose buds to lavender pink flowers rather than orange buds to pink flowers.

This plant exhibits the following characteristics that make it unique:

1. rose buds to lavender pink flowers in large inflorescences,
2. a long bloom time,
3. a short, compact habit, and
4. good cold tolerance,
5. excellent vigor.

The new variety has been reproduced only by asexual propagation (stem cuttings and micropropagation using apical buds and nodes). Each of the progeny exhibits identical characteristics to the original plant. Asexual propagation by stem cuttings and micropropagation using apical buds and nodes as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows an 18-month-old plant of the new cultivar grown in a trial garden in full sun in early July in Canby, Oreg.

DETAILED PLANT DESCRIPTION

The following is a detailed description of the new *Agastache* cultivar based on observations of 18-month-old specimens in mid-July growing in full sun in a garden in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on The Royal Horticultural Society Colour Chart, 5$^{th}$ edition, 2007.

Plant:

*Form*.—Upright, bushy.
*Type*.—Herbaceous perennial.
*Cold hardiness*.—USDA Zone 6-10.
*Size*.—Grows to 50 cm wide and 40 cm tall to the top of the flowers.
*Vigor*.—Excellent.
*Branching*.—About 15 main stems from the base, these branch at every node.
*Stem*.—Square in cross section, grows to 4 mm wide and 28 cm tall to the first flower, pubescent, Yellow Green 147B, internodes range from 1 cm to 4 cm long.
*Roots*.—White 155B, fibrous, plants root easily from stem tip cuttings.

Leaf:

*Type*.—Simple.

*Arrangement*.—Opposite.

*Shape*.—Broadly ovate to ovate.

*Venation*.—Pinnate.

*Margins*.—Coarsely serrate.

*Apex*.—Acute.

*Base*.—Cuneate to auriculate.

*Blade size*.—Grows to 33 mm long and 30 mm wide.

*Surface texture*.—Pubescent on both sides.

*Petiole description*.—Grows to 15 mm long and 2 mm wide, pubescent, Yellow Green 147C.

*Leaf color*.—Top side Green N137A with vein Yellow Green 147C, bottom side closest to Yellow Green 147B with vein 147C.

*Fragrance*.—Aromatic.

Inflorescence:

*Type*.—Terminal spike with up to 14 congested whorls.

*Number of flowers*.—Up to 600 per spike.

*Size of inflorescence*.—Grows to 20 cm tall and 3 cm wide.

*Peduncle*.—Grows to 4 cm tall and 2.5 mm wide, pubescent, Yellow Green 146C.

*Pedicel*.—Grows to 1.5 mm long, pubescent, Yellow Green 146C.

*Bloom period*.—June through frost in Canby, Oreg. (with better repeat bloom if plants are cut back after main bloom).

Flower bud:

*Size*.—13.5 mm long and 3 mm wide at the widest point prior to opening.

*Description*.—Tubular.

*Surface texture*.—Pubescent.

*Color*.—Red Purple 70A.

Flower:

*Type*.—Zygomorphic.

*Shape*.—Bilabiate, tubular.

*Size*.—20 mm long and 8 mm wide.

*Corolla description*.—17 mm long and spreads to 8 mm wide; outside and inside Purple 77C, pubescent inside and out, tube 15 mm long and 1 mm to 4 mm wide; 2 upper lobes joined, each 3 mm long and 4 mm wide, each oblong, tips obtuse, margins entire; three lower lobes, two spreading sideways and curl back, each 2 mm long and 2 mm wide, tip acute, margin irregular to entire; bottom lobe, strongly reflexed, broadly reniform, notched at the tip, margin irregularly crenulate, 5 mm wide and 3 mm deep.

*Calyx description*.—Campanulate, 7 mm long and 3 mm wide, pubescent inside and out, 5 lobed, lobes lanceolate, 2 mm long and 1 mm wide, entire, acute, Greyed Orange 165.

*Pistil description*.—21 mm long, ovary 1 mm long and 1 mm wide, Yellow Green 147C, style 19 mm long, White NN155A blending to Purple 70A near stigma, stigma two-parted, 1 mm deep, Purple 70A.

*Stamen description*.—4 in number, paired and exerted, top two 8 mm long and bottom two 10 mm long, filaments Purple Violet N80C, anthers 0.5 mm long, Purple N77A, pollen White NN155A.

*Fragrance*.—Aromatic.

*Lastingness*.—A spike blooms for about 4 weeks on the plant.

Fruit/seed: 4 nutlets, 1 mm long, ovoid, Black 202A.

Pests and diseases: The new cultivar is typical to the genus. No known resistances to pests or diseases. No problems have been found in Canby, Oreg.

I claim:

1. A new and distinct form of *Agastache* plant substantially as shown and described.

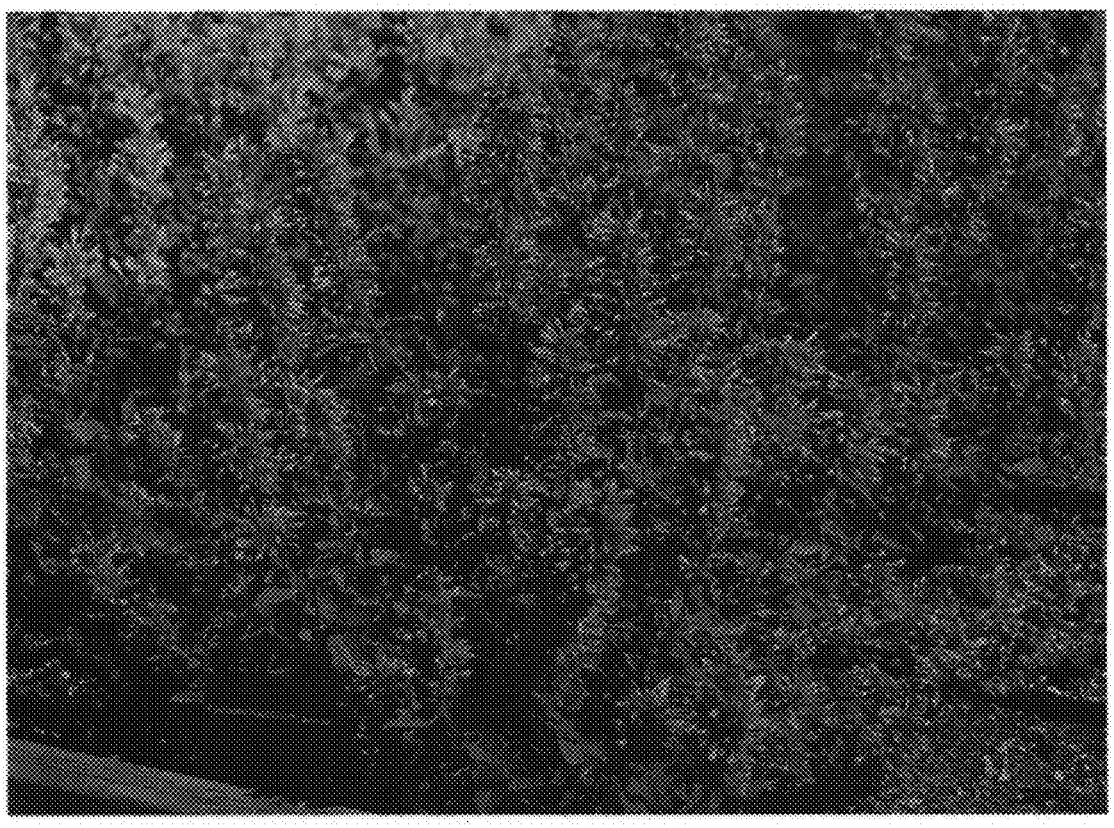

* * * * *